United States Patent [19]

Baker, Jr. et al.

[11] Patent Number: 4,821,723
[45] Date of Patent: Apr. 18, 1989

[54] BIPHASIC WAVEFORMS FOR DEFIBRILLATION

[75] Inventors: Ross G. Baker, Jr., Houston; Stephen J. Whistler, Lake Jackson, both of Tex.; Raymond E. Ideker, Durham, N.C.; Richard V. Calfee, Houston; Edward A. Haluska, Angleton, both of Tex.

[73] Assignee: Intermedics Inc., Angleton, Tex.

[21] Appl. No.: 19,705

[22] Filed: Feb. 27, 1987

[51] Int. Cl.$^4$ .................. A61N 1/00; H05G 00/00
[52] U.S. Cl. ................................................. 128/419 D
[58] Field of Search ................... 128/419 PG, 419 D

[56] References Cited

U.S. PATENT DOCUMENTS

| | | | |
|---|---|---|---|
| 3,746,006 | 7/1973 | Thaler | 128/419 PG |
| 3,924,641 | 12/1975 | Weiss | 128/419 PG |
| 4,168,711 | 9/1979 | Cannon, III et al. | 128/419 D |
| 4,327,322 | 4/1982 | Yukl | 128/421 |
| 4,595,010 | 6/1986 | Radke | 128/421 |
| 4,637,397 | 1/1987 | Jones et al. | 128/419 D |

OTHER PUBLICATIONS

Schuder et al., "Waveform Dependency in Defibrillating 100 kg Calves," *Devices & Tech. Meeting*, NIH, 1982; p. 174.

J. L. Jones & R. E. Jones, "Defibrillator Waveshape Optimization," *Devices & Tech. Meeting*, NIH, 1982; p. 175.

Schuder et al., "Ultrahigh-Energy Hydrogen Thyratron/SCR Bidirectional Waveform Defibrillator," *Medical & Biological Engineering & Computing*, Jul. 1982, pp. 419–424.

Schuder et al., "Development of Automatic Implanted Defribrillator," *Devices & Tech. Meeting*, NIH; p. 206, (1981).

Tang et al., "Ventricular Defibrillation Using Biphasic Waveforms of Different Phasic Duration," *PACE*; vol. 10, Mar.-Apr. 1987.

Tang et al., "Strength Duration Curve for Ventricular Defibrillation Using Biphasic Waveforms," *The North Amer. Society of Pacing and Electrophysiology*; May 2, 1987; p. 49.

L. A. Geddes, Cardiovascular Devices and Their Applications, 1984, 300–319.

*Primary Examiner*—Francis Jaworski
*Assistant Examiner*—George Manuel
*Attorney, Agent, or Firm*—Russell J. Egan; Donald R. Greene

[57] ABSTRACT

In a method and apparatus for defibrillating a heart in fibrillation, the onset of fibrillation of the heart is detected, and a biphasic waveform having only a first phase and a second phase is applied to the fibrillating heart. Each phase of the waveform is characterized by a predetermined time duration and by a predetermined polarity and magnitude of voltage, the duration of the first phase being greater than the duration of the second phase, and the initial voltage magnitude of the first phase being greater than that of the second phase. The biphasic waveform is applied by delivering it to a pair of patch electrodes affixed over and contoured to conform substantially to the surface of the right and left ventricles, respectively. The patch electrodes are affixed to either the epicardium or the pericardium. The left ventricular patch electrode is used as the cathode for the first phase of the applied biphasic waveform, and as the anode for the second phase. No further shocks are delivered to the heart pending detection of cardiac activity in response to the shocks delivered by the application of the biphasic waveform.

16 Claims, 10 Drawing Sheets

HIGH VOLTAGE GENERATION & OUTPUT SECTION (& DEVICE OUTPUT TERMINALS)

TRANSFORMER ISOLATED SWITCH DRIVER CIRCUIT

OUTPUT
SHORT CIRCUIT
PROTECTION

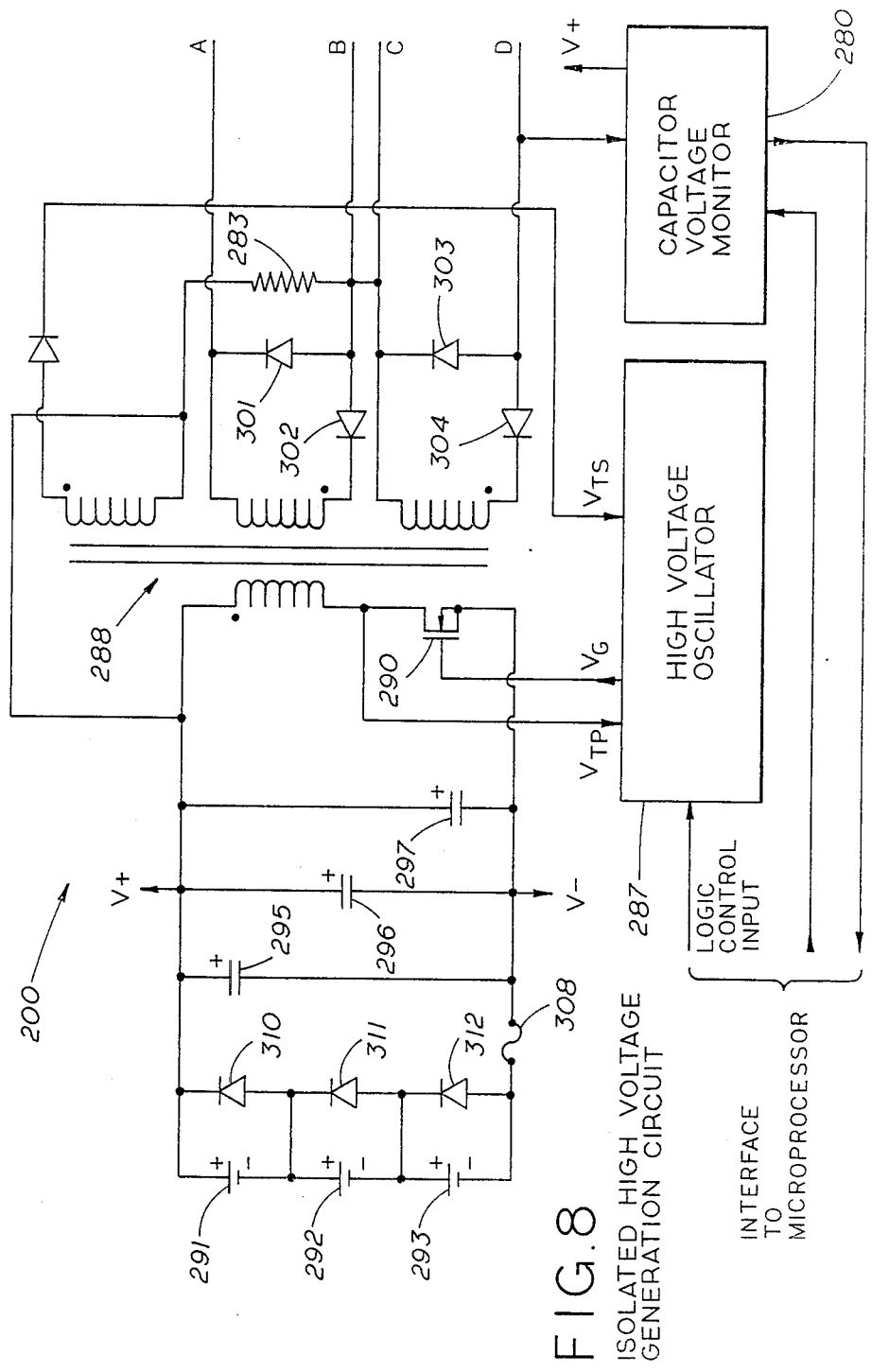
FIG. 8 ISOLATED HIGH VOLTAGE GENERATION CIRCUIT

HIGH VOLTAGE OSCILLATOR

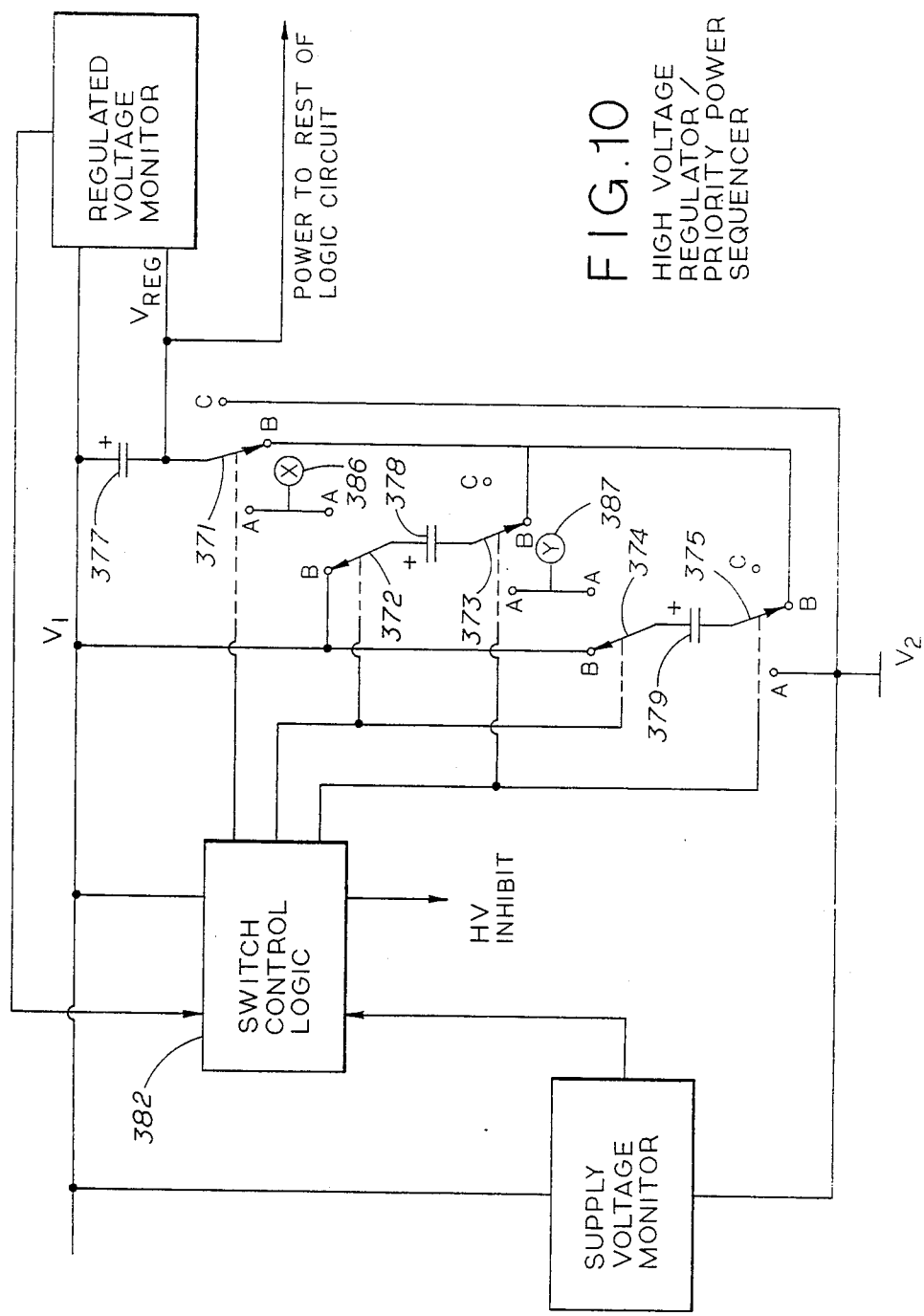
FIG. 10 HIGH VOLTAGE REGULATOR/PRIORITY POWER SEQUENCER

BIPHASIC WAVEFORMS FOR DEFIBRILLATION

BACKGROUND OF THE INVENTION

1. Field of the Invention

The present invention relates generally to methods and apparatus for cardiac defibrillation, and more particularly to the use of biphasic waveforms of a specific configuration in conjunction with such methods and apparatus.

2. Relevant Background

Cardiac arrhythmias can arise in the atrial or ventricular chambers as a consequence of an impairment of the heart's electro-physiologic properties such as excitability, conductivity, and automaticity (rhythmicity). Tachycardia is an arrhythmia characterized by rapid beating of the affected chamber which, in some instances, may lead to fibrillation. In other instances, fibrillation may arise in a diseased heart without the advance episode of a tachyarrhythmia.

During fibrillation, sections of conductive cardiac tissue of the affected chamber undergo completely uncoordinated random contractions, quickly resulting in a complete loss of synchronous contraction of the overall mass of tissue and a consequent loss of the blood-pumping capability of that chamber. Because of the lack of contribution of the atrial chambers to cardiac output, atrial fibrillation is hemodynamically tolerated and not generally regarded as life-threatening. However, in the case of ventricular fibrillation, cardiac output ceases instantaneously as a result of the rapid, chaotic electrical and mechanical activity of the excitable myocardial tissue and the consequent ineffectual quivering of the ventricles. Unless cardiac output is restored almost immediately after the onset of ventricular fibrillation, tissue begins to die for lack of oxygenated blood, and death will occur within minutes.

Since ventricular fibrillation is frequently triggered by acceleration of a ventricular tachycardia, various methods and devices have been developed or proposed to treat and arrest the tachycardia before the onset of fibrillation. Conventional techniques for terminating tachycardia include pacing therapy and cardioversion. In the latter technique, the heart is shocked with one or more current or voltage pulses of generally considerably higher energy content than is delivered in pacing pulses. Unfortunately, the therapy itself presents a considerable risk of precipitating fibrillation.

Defibrillation—that is, the method employed to terminate fibrillation—generally involves applying one or more high energy "countershocks" to the heart in an effort to overwhelm the chaotic contractions of individual tissue sections and to re-establish an organized spreading of action potential from cell to cell of the myocardium, thereby restoring the synchronized contraction of the mass of tissue. If these chaotic contractions continue in any tissue section, the defibrillation may be short-lived in that the uncontrolled tissue section remains a potential source for re-fibrillation. Successful defibrillation clearly requires the delivery of a shocking pulse containing a substantial amount of electrical energy to the heart of the afflicted person, at least adequate to terminate the fibrillation and to preclude an immediate re-emergence. Although high intensity defibrillation shocks are often successful in arresting fibrillation, they tend to precipitate cardiac arrhythmias, which themselves may accelerate into fibrillation. Moreover, the high intensity shocks can cause permanent myocardial injury.

In the conventional approach of transthrracic external defibrillation, paddles are positioned on the patient's thorax and, typically from about 100 to 400 joules of electrical energy is delivered to the chest area in the region of the heart. It is apparent that, from the manner in which the shock is applied, only a portion of this energy is actually delivered to the heart and, thus, is available to arrest fibrillation. Where fibrillation occurs during open heart surgery, internal paddles may be applied to opposite surfaces of the ventricular myocardium and, in these instances, the energy required to be delivered is considerably less, on the order of 20 to 40 joules.

More recently, implantable automatic defibrillators have been developed for use in detecting and treating ventricular fibrillation. In 1970, M. Mirowski et al. and J. O. Schuder et al. separately reported in the scientific literature their independent proposals for a "standby automatic defibrillator" and a "completely implanted defibrillator", respectively, including experimental results in dog tests. Since that time, a vast number of improvements in implantable defibrillators, including fibrillation detectors and high energy pulse generators with related electrode configurations, have been reported in the scientific literature and the patent publications.

The pulse energy requirements for internal defibrillation with known implantable defibrillators and electrode systems range from about 5 joules to approximately 40 joules. Of course, the actual energy level required may differ from patient to patient, and further depends on such factors as the type of pulse waveform and the electrode configuration employed. While advances and improvements in electrical energy sources in general and pacemaker batteries in particular have been made over the past few years, It is clear, nonetheless, that repeated delivery of such amounts of energy from an implanted system will deplete conventional batteries in relatively short order. Accordingly, for this and other reasons mentioned above, reduction of energy level required for internal defibrillation remains a key area of inquiry and investigation.

It is a principal object of the present invention to provide improvements in methods and apparatus for the generation and application of shocking waveforms effective for either internal or external defibrillation.

A related object is to provide methods and apparatus for generating and applying improved configurations of biphasic waveforms, usable preferably in conjunction with implantable automatic defibrillators but alternatively for external defibrillation. We have found these improved configurations to be effective in terminating fibrillation with delivery of considerably less energy than has been necessary using prior art systems and methods.

Prior proposed implantable defibrillators have commonly employed systems to produce unidirectional (also referred to as unipolar) shocking pulses, as for example, are described in U.S. Pat. Nos. Re. 30,372 to Mirowski et al., Re. 30,387 to Denniston et al., and 4,210,149 to Heilman et al. Some have suggested that the delivery of a sequence of unidirectional high intensity pulses by the implanted defibrillator is somewhat more effective. More recent studies have indicated that bidirectional (or biphasic) waveforms may decrease required defibrillation shock strengths and reduce post-shock cardiac arrhythmias. In the latter respect, exemplary publications include those of J. L. Jones et al., "Improved defibrillator waveform safety factor with biphasic waveforms," Am J Physiol 245 (Heart Circ Physiol 14): H60, 1983; "Decreased defibrillator-induced dysfunction with biphasic rectangular waveforms," Am J Physiol 247 (Heart Circ Physiol 16): H792, 1984; and "Reduced excitation threshold in potassium depolarized myocardial cells with symmetrical biphasic waveforms," J Mol Cell Cardiol 17: XXVII, 1985; and those of J. C. Schuder et al., "Transthoracic ventricular defibrillation in the 100 kg calf with symmetrical one-cycle bidirectional rectangular wave stimuli," IEEE Trans Biomed Eng 30: 415, 1983; and "Defibrillation of 100-kg calves with asymmetrical, bidirectional, rectangular pulses," Cardiovasc Res 419, 1984.

SUMMARY OF THE INVENTION

The present invention provides improvements in implantable automatic defibrillators, in terms of the types of waveforms generated and applied to the heart; and improvements in methods of defibrillation, again in terms of the defibrillating waveforms. According to the invention, the defibrillation threshold, that is to say, the level of voltage (or current), and total energy, at which successful internal defibrillation is achieved, is substantially reduced relative to the thresholds obtained using prior art techniques, apparatus and methods, by utilizing a biphasic shock having an initial phase whose duration is at least slightly greater than the duration of the second phase. The biphasic waveform having such phase durations is delivered to the ventricular myocardium, preferably with an implanted defibrillator but alternatively using a defibrillator external to the patient.

In another aspect of the invention, the longer duration first phase of the biphasic waveform commences with a voltage magnitude equal to or greater than the initial voltage level of the second phase.

According to a further aspect of the invention, a preferred embodiment of an implantable automatic defibrillator includes a fibrillation detector, a biphasic waveform generator for providing the biphasic shocks in which the first phase is greater than the second phase, patch electrodes affixed over the epicardial or pericardial surfaces of the left and right ventricles, and electrically conductive leads for delivering the biphasic waveform to the electrodes. The patch electrodes are specially configured to provide a more uniform potential gradient field through the ventricular myocardium.

The size of an implantable automatic defibrillator is largely determined by the sizes of the batteries and capacitors. A reduction in the shock strength heretofore required for defibrillation allows the use of smaller sizes of those critical components and the design of implantable defibrillators of commensurately smaller size. Moreover, a decrease in the shock strength necessary to achieve direct defibrillation appears likely to reduce the threat and extent of myocardial damage, and the possibility of induced cardiac arrhythmias, which can be caused by high intensity defibrillation shocks, as well as the extent of discomfort to the patient with false shocks. Implantable automatic defibrillators of smaller size also make it more feasible to implant the device in the patient's chest area rather than in the lower abdomen. In addition to the desirable cosmetic effect, implantation in the chest region better positions the device for use with transvenous electrodes which may become available for defibrillation. Accordingly, it is another object of the present invention to achieve all of those desirable objectives associated with lower defibrillation thresholds and smaller size of the implantable defibrillator.

BRIEF DESCRIPTION OF THE DRAWINGS

The above and still further objects, features and attendant advantages of the present invention will become apparent to those persons skilled in the field to which the invention pertains from a consideration of the following detailed description of a presently preferred embodiment, taken in conjunction with the accompanying drawings, in which.

DETAILED DESCRIPTION OF A PREFERRED EMBODIMENT

Figure 1A:
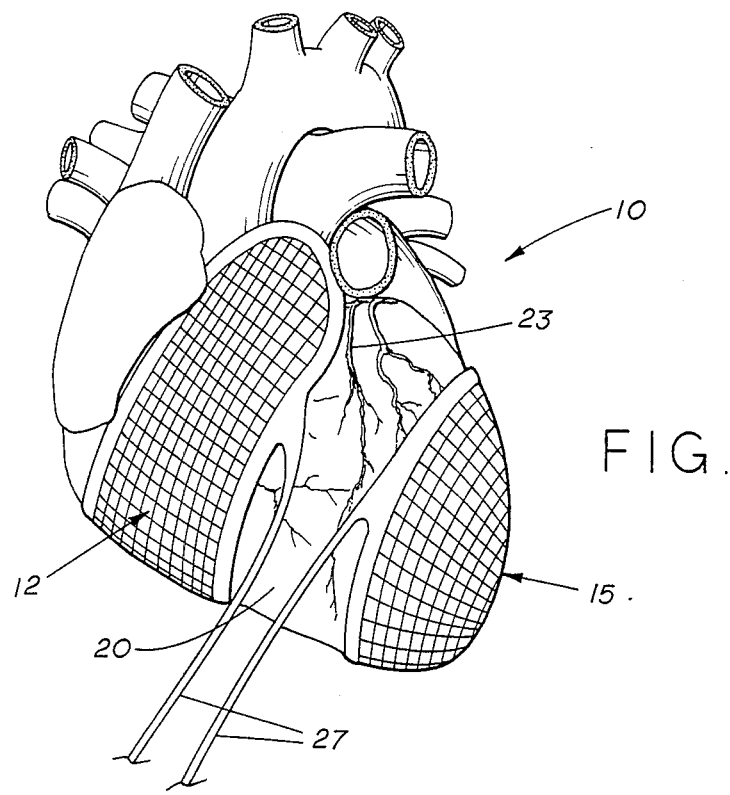
FIGS. 1a and 1b are diagrammatic representations of contoured patch electrodes preferably employed in practicing the invention, from anterior and posterior views of the heart, respectively.

As noted in the "Background" section above, investigators have proposed various waveforms for use in defibrillation and there remains some considerable disagreement as to which of these are more effective. An implantable defibrillator described by Mirowski et al. in 1982 ("The automatic implantable defibrillator; new modality for treatment of life-threatening ventricular arrhythmias," Pace 5: 384) utilized a single truncated exponential waveform described by Schuder et al. ("Transthoracic ventricular defibrillation with triangular and trapezoidal waveforms," Circ Res 19: 689, 1966). Several investigators have asserted that multiple monophasic defibrillation shocks appear to be more effective than single monophasic shocks. Supporting results for that proposition are reported, for example, by J. D. Bourland et al. in "Sequential pulse defibrillation for implantable defibrillators," Med Instrum 20: 138, 1986; and by D. L. Jones et al. in "Improved internal cardiac defibrillation in man using sequential pulse countershock energy delivery," J Am Coll Cardiol 5: 457, 1985 (abstract), and "Internal cardiac defibrillation in man: Pronounced improvement with sequential pulse delivery to two different lead orientations," Circulation 73: 484, 1986. However, others have found no advantage in multiple monophasic shocks over single monophasic shocks in terms of energy requirements for defibrillation. Reference may be made, for example, to articles by L. A. Geddes et al., "Ventricular defibrillation with single and twin pulses of half sinusoidal current," J Appl Physiol 34: 8, 1973; and by Schuder et al., "Transthoracic ventricular defibrillation in the dog with unidirectional rectangular double pulses," Cardiovasc Res 4: 497, 1970.

As further noted earlier herein, recent investigations have shown that biphasic waveforms are superior to monophasic waveforms in many cases. In reported experiments in an article referenced in the above "Background" section, Schuder and his associates were able to defibrillate 100 Kg calves using symmetrical biphasic rectangular waveforms at a lower range of energy and current, and to achieve a higher percentage of successful first shock defibrillations than with monophasic waveforms. Those same investigators obtained good results with asymmetrical biphasic waveforms in which the amplitude of the second phase of the shock was smaller than that of the first phase, and the two phases were of equal duration.

As reported in another of the above-referenced articles (J Mol Cell Cardiol 17: XXVII, 1985), J. L. Jones and associates found that biphasic waveforms in which the second phase was of lower amplitude than the first phase decreased post-shock dysfunction in cultured myocardial cells. The mechanism they proposed to explain the success of biphasic waveforms relates to their finding that biphasic waveforms reduced the excitation threshold of potassium-depolarized chick embryo myocardial cells when compared to the excitation threshold found with monophasic waveforms. This reduction in excitation threshold occurred for biphasic waveforms of 2-40 milliseconds total duration, but not for shorter durations. Jones et al. hypothesized that since extracellular potassium is decreased during fibrillation and the resting potential is reduced to about −60 millivolts, the first phase of the biphasic waveform may act as a "conditioning" pulse in that it causes hyperpolarization of a portion of the cells. Hyperpolarization would return the resting potential to a more normal value and lower excitation threshold.

We theorized that if such a conditioning mechanism does indeed function, the duration of the first phase of the biphasic waveform may have a significant effect on the extent of the conditioning. The present invention is based on that proposition and on the results of experimentation performed on test dogs. Our findings were that we were able to reduce defibrillation threshold energy levels by 70% or more from the previous lowest levels generally reported by others, by using biphasic waveforms in which the first phase is of greater duration than the second phase, or, stated another way, in which the first phase duration is greater than half of the total shock duration.

Successful internal defibrillation in humans and in dogs generally requires energy levels in the 5 to 25 joule range, according to the values reported by most investigators. We have been able to achieve reliable and consistent defibrillation in test dogs in a range below 2 joules, and as low as 0.64 joule, utilizing biphasic waveforms in accordance with the present invention. It appears that a short first phase, relative to the second phase, may be of insufficient duration to allow a conditioning process to be completed. However, we are not certain of the precise reasons for this consistently successful internal defibrillation with a substantial reduction in shock strength, and accordingly, we do not wish to have the invention constrained to that particular theory.

According to another aspect of the present invention, the initial phase of the defibrillation shock should preferably be of higher voltage than or at least equal to the voltage level of the following phase (disregarding, for the moment, the voltage decay as the capacitors are connected to the load during the initial phase, and with no recharging before commencing the second phase). We have found that a higher voltage first phase, in conjunction with the longer duration of that phase, assists in resuscitation with lower shock intensity than is achieved with biphasic waveforms where the first phase is of longer duration but lower magnitude than the second phase. Here again, we are not certain of the reasons for this beneficial effect, but it may be that a lower voltage first phase generates insufficient current flow to condition the myocardial cells.

A further aspect of the invention involves the preferred use of large surface area defibrillation patch electrodes of the type disclosed in the copending U.S. patent application Ser. No. 019,670 of R. E. Ideker et al. entitled "Implantable Defibrillation Electrodes", which was filed on the same date as the instant application and is assigned to the same assignee. For the sake of convenience to the reader, some of the disclosure of that copending application is repeated herein, but reference should be made to the entire disclosure of that application for ancillary details of the structure of the patch electrodes. In an embodiment used in our tests, the electrodes were contoured to match the general shape of the endocardium or the pericardium in the region of the left and right ventricles of the heart, depending respectively on whether they were to be secured to the endocardium or the pericardium over the ventricles. Before proceeding further, it should be emphasized that although it appears these electrodes played an important role in the results achieved, they appear to have been secondary to the significance of the particular configuration of the biphasic waveform utilized for the defibrillating shock. This will be explained in more detail presently, in the examination of the histograms of FIGS. 2 and 3.

Figure 1B:
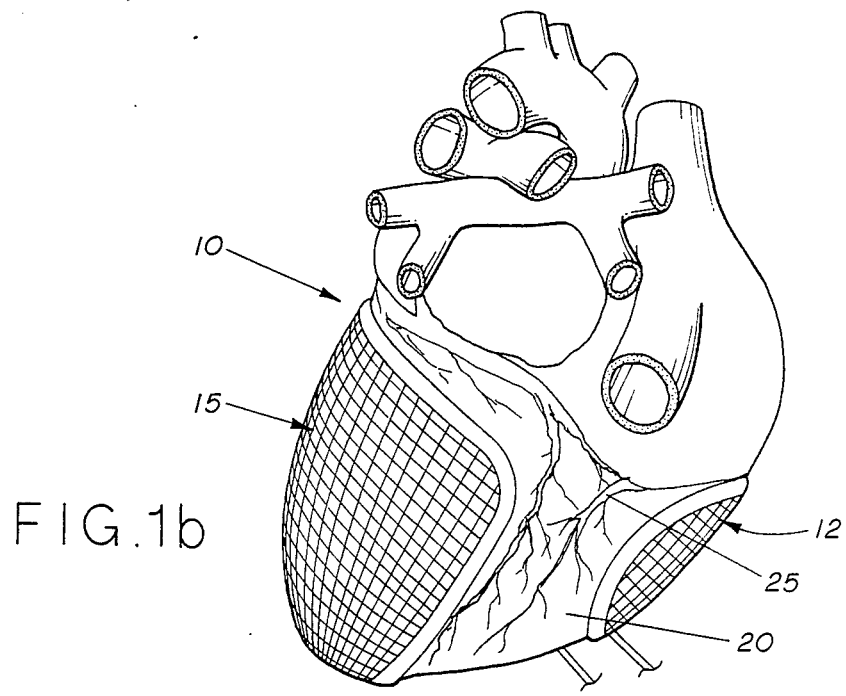

Referring first to FIGS. 1a and 1b, a pair of contoured defibrillation patch electrodes 12 and 15 are configured with relatively large surface area to encompass the regions of the left and right ventricles. Viewed from the anterior as shown in FIG. 1a, the right ventricular patch electrode 12 is mostly anterior, extending from just below the right atrium and nearly covering the right ventricle to a point short of the posterior descending coronary artery, middle cardiac vein and interventricular septum, extending to the beginning of the pulmonary trunk. The left ventricular patch electrode 15 is mostly posterior, covering most of the left ventricle and extending from just beneath the left atrium to a point short of the posterior descending coronary artery, middle cardiac vein and interventricular septum, and forming a cup around the apex of the heart 10. Each electrode is fabricated from a suitable conductive mesh, such as titanium, with a flexible conformal biocompatible insulative backing layer, such as silicone rubber, with the conductive mesh lying closest to the heart when the respective electrode is secured in place for delivering the defibrillating biphasic waveforms to the ventricular myocardium.

The two patch electrodes 12, 15, when in place over the respective ventricles, encompass a substantial portion of the ventricular myocardium. It is believed that this establishes a more uniform potential gradient field throughout the entire ventricular mass than is achieved with other types of defibrillating electrodes, including other configurations and placements of patch electrodes. In addition, the gap 20 between confronting edges of the two patch electrodes is maintained relatively uniform throughout the region of the confrontation, and is sufficiently wide to eliminate or considerably reduce the likelihood that current will be shunted between the confronting electrode edges when defibrillating shocks are applied. Further, as noted above, this substantially equidistant spacing between the confronting borders of the two patches is of sufficient width to accommodate the interventricular septum and some of the major coronary arteries, such as the left anterior descending coronary artery 23 and the posterior descending coronary artery 25. This tends to assure that the current flow will be through one ventricle across the septum to the free wall of the other ventricle, rather than along the high conductivity blood cavities of the ventricles, and also to reduce the possibility of vascular damage, during application of the high voltage defibrillating shocks to the electrodes.

Separate low impedance coil leads 27, of tantalum-wrapped zirconium copper alloy which is drawn through a die (this particular coil wire being available from Heraeus of West Germany), for example, are electrically connected to the conductive mesh of the respective patch electrodes at a point such that each lead will be disposed at and preferably descend from the anterior of the heart when the electrodes are positioned in the manner described above. Each lead 37 is provided with a connector terminal (not shown) in a conventional manner to permit its connection to an implantable defibrillator (not shown).

Figure 2:
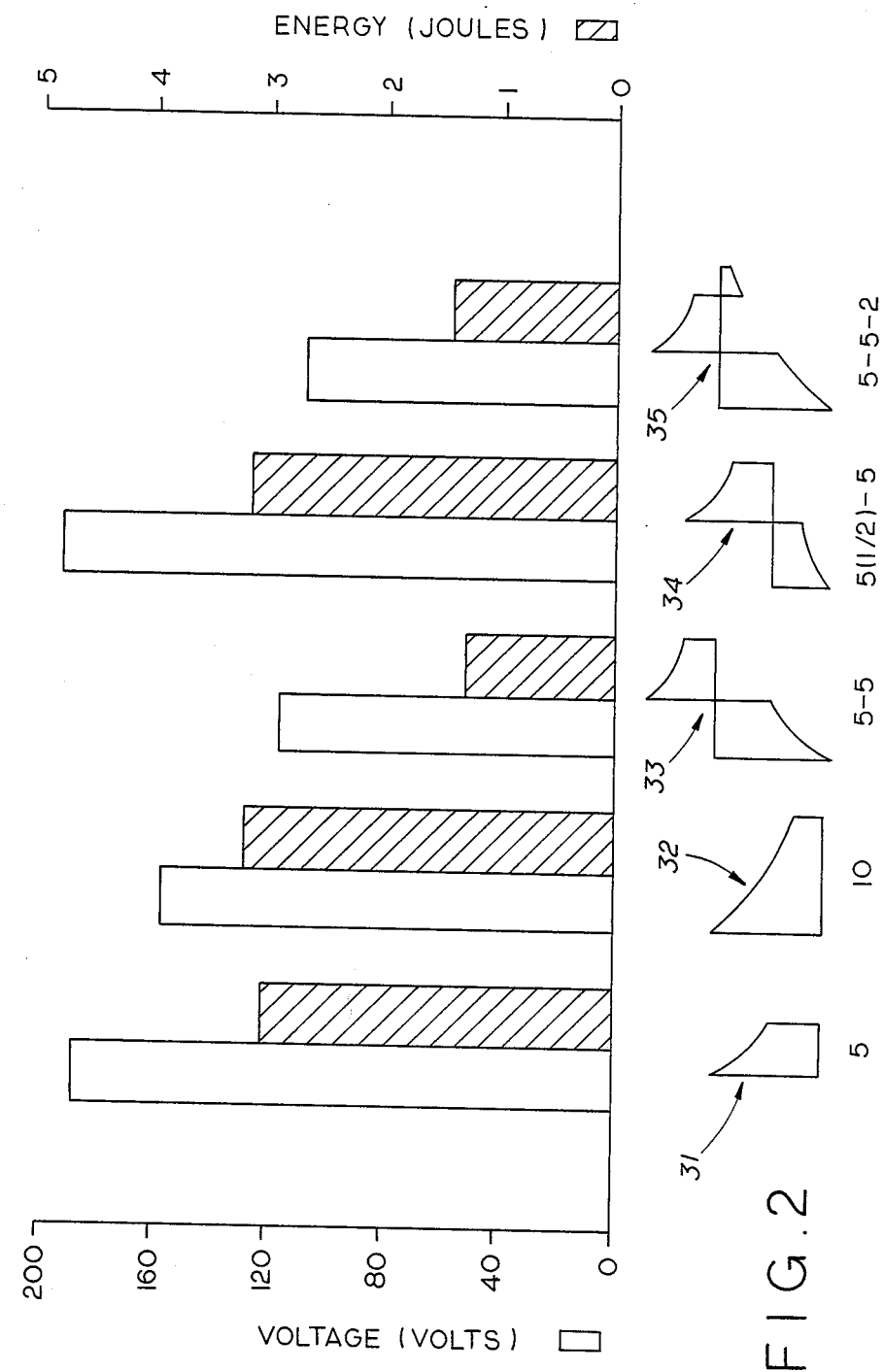
FIG. 2 is a set of histograms of defibrillation threshold voltage and energy for five waveforms applied epicardially, using the patch electrodes of FIG. 1, in experiments conducted on six test dogs, the diagrams of the respective waveforms being shown at the bottom of FIG. 2.
Figure 3:
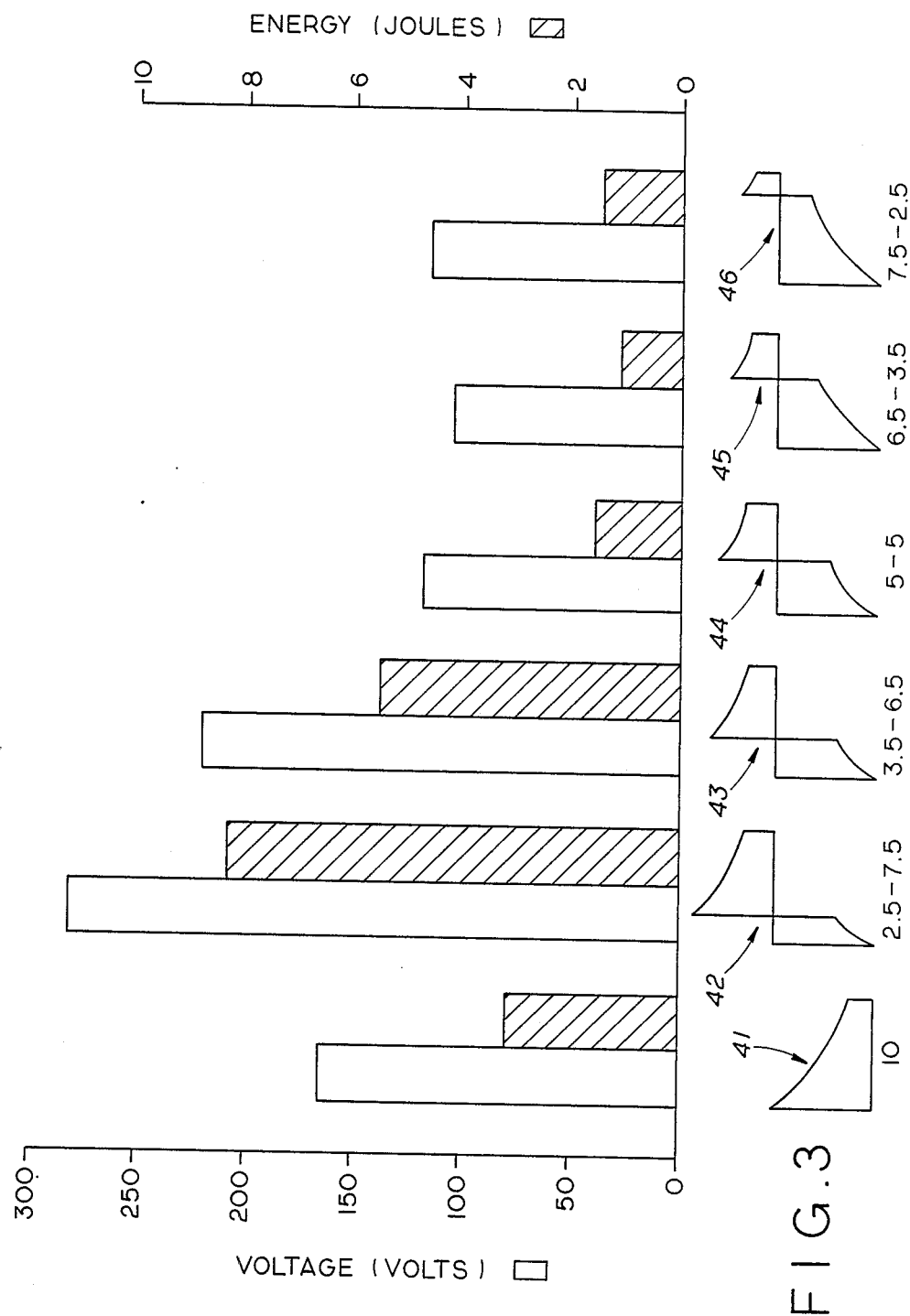
FIG. 3 is a set of histograms similar to FIG. 2, but in which six different waveforms (shown at the bottom of the FIG.) were applied pericardially using the patch electrodes of FIG. 1, in experiments conducted on another six test dogs.

Referring now to FIGS. 2 and 3, each of which is a set of histograms of defibrillation threshold voltage and energy for selected defibrillation waveforms, the FIG. 2 histograms were obtained using epicardial electrode placement and waveform application, and the FIG. 3 histograms were obtained with pericardial electrode placement and waveform application. The results shown in each of these sets of histograms are from tests performed on separate groups of six mongrel dogs each. The particular waveforms used to obtain the results are depicted below the respective histograms in the two Figures. The total duration of each of the defibrillation waveforms is indicated beneath its respective depiction. To allow for the possibility that the patch electrodes secured to the epicardium in each of the first six test dogs might interfere with wall motion, tests were also conducted on a second set of six test dogs with patch electrodes secured to the pericardium.

Referring to FIG. 2, defibrillation thresholds were determined using five different waveforms 31-35 applied epicardially: waveform 31, a monophasic shock of five milliseconds duration; waveform 82, a monophasic shock of ten milliseconds duration; waveform 33, a biphasic shock of ten milliseconds total duration, with both phase durations equal to five milliseconds; waveform 84, a biphasic shock of ten milliseconds total duration, with both phase durations equal to five milliseconds and with the first phase delivered at one-half the voltage at which the second phase is delivered; and waveform 35, a triphasic shock with phase durations of five, five and two milliseconds, respectively After ventricular fibrillation was induced, an initial shock of 100 volts was applied during diastole of normal sinus rhythm for the first dog in the series, and the impedance of the heart was calculated. The defibrillation sequence was then begun with a shock of approximately four joules for each of waveforms 31-35. In subsequent dogs, the average defibrillation threshold of previous dogs for each waveform was used as the initial shock voltage. If defibrillation was successful, the strength of the next defibrillation shock was decreased by 20 volts, and by the same amount for subsequent shocks until a defibrillation attempt failed. The strength of the shock was then increased by ten volts and the lowest shock which achieved defibrillation was considered to be the defibrillation threshold.

If the initial shock failed to defibrillate, a salvage shock of known high effectiveness was given within 30 seconds of the onset of ventricular fibrillation. Subsequent defibrillation shocks given after re-inducing episodes of ventricular fibrillation were increased in increments of 20 volts until defibrillation was achieved. The shock strength was then decreased by ten volts and the lowest voltage which successfully defibrillated was designated as the defibrillation threshold. A recovery period of at least five minutes was provided between each episode of fibrillation.

The order in which waveforms 31-35 were tested was rotated for each of the six dogs. The shocks were truncated exponential waveforms delivered from a 175 microfarad capacitor, except for the first phase of waveform 34 which was delivered from a 350 microfarad capacitor. For the shocks delivered from the 175 microfarad capacitor through a 40 ohm impedance, the waveform tilt (droop) was about 50% for a five millisecond shock and about 75% for a ten millisecond shock (referring in each case to total duration of the shock). Particular embodiments suitable for delivery of the biphasic waveforms will be described presently. The left ventricular electrode was the anode for the monophasic shocks; the cathode and then the anode for the biphasic shocks; and the cathode, the anode, and the cathode for the triphasic shocks. Switch time between phases of multiphasic shocks was 0.12 milliseconds, but this is not significant—the time between phases may be considerably less. For the biphasic waveform 34 and triphasic waveform 35, the energy of each shock was calculated from the measured leading and trailing edge voltages of the waveform and from the impedance at the beginning of the phase for which the left ventricular electrode was the anode. For biphasic waveform 34, the energy was calculated from the measured leading edge voltage, the value of capacitance appropriate for each phase, and the impedance measured at the leading edge of the second phase.

It will be observed from FIG. 2 that the defibrillation thresholds expressed as voltage were lower for the biphasic waveform 33 in which the initial voltage level of the first phase is higher than the initial voltage level of the second phase, and for the triphasic waveform 35, than the defibrillation threshold voltages of the monophasic waveforms 31 and 32 and the biphasic waveform 34 in which the initial voltage level of the first phase is half that of the second phase. More specifically, the defibrillation threshold voltages for full voltage biphasic waveform 33 and triphasic waveform 35, each with equal duration first and second phases, were significantly lower (at approximately 105 volts each) than that for the longer duration monophasic waveform 32 (at about 160 volts), which itself was significantly lower than the defibrillation threshold voltages for the shorter duration monophasic waveform 31 (at about 190 volts) and the half voltage biphasic waveform 34 (at approximately 200 volts). Expressed in terms of energy, the defibrillation thresholds for the full voltage biphasic waveform 38 and the triphasic waveform 35, both with equal first and second phase durations, were at or about 1.5 joules.

Referring now to FIG. all of the defibrillation waveforms selected for pericardial application were biphasic except for one which was monophasic. All waveforms had a total duration of ten milliseconds, but, having determined the efficacy of biphasic waveforms in the epicardial application, the biphasic waveforms were chosen here to have different relative durations of the two phases. Of these six pericardially-applied waveforms 41–46: waveform 41 is monophasic, and waveforms 42–46 are biphasic in which the relative durations of the first and second phases are 2.5 and 7.5, 8.5 and 6.5, 5 and 5, 6.5 and 8.5, and 7.5 and 2.5 milliseconds, respectively. Defibrillation thresholds were determined by the same procedure as that described with respect to the test dogs for the results in FIG. 2. Here again, a recovery period of at least five minutes was provided between successive episodes of fibrillation, and the order of application of the waveforms was rotated for each test dog.

It will be observed from FIG. 3 that the defibrillation thresholds expressed in terms of either voltage or energy were significantly lower for biphasic waveforms 44–46, in which the duration of the first phase was equal to or greater than the duration of the second phase, than those of the other waveforms 41–43. The defibrillation thresholds for the shorter relative duration biphasic waveforms 42 and 43 were much higher than that of even the monophasic waveform 41. In contrast, the defibrillation threshold for biphasic waveform 45 was less than two joules in all six dogs. No significant difference was found in defibrillation threshold voltage or energy for epicardial and pericardial application of identical biphasic waveforms 43 (FIG. 2) and 44 (FIG. 3).

In each instance, the cathode for the first phase is preferably the larger electrode (the left ventricular patch), to minimize impedance, assuming that the first phase is the larger voltage.

Further experiments on test dogs have yielded successful defibrillation with mean threshold energy levels as low as 0.64 joule using biphasic waveforms with 3.5-1 and 3.5-2 first phase-second phase durations (in milliseconds), subject to standard deviation of plus or minus 0.21 and 0.27, respectively. In each instance, the better results were achieved where the first phase had a duration at least slightly greater than the duration of the second phase.

A preferred embodiment of apparatus for providing the biphasic waveforms according to the present invention is that described as the high voltage defibrillator section in the copending U.S. patent application Ser. No. 875,218 of Haluska et al., entitled "Implantable Cardiac Stimulator for Detection and Treatment of Ventricular Arrhythmias", filed June 17, 1986 (hereinafter referred to as "copending application 875,218"). Alternatively, the biphasic waveform generator described in copending U.S. patent application Ser. No. 847,283 of Winstrom, entitled "Apparatus for Generating Biphasic Defibrillation Waveform", filed Apr. 2, 1986 may be used. Each of those applications is assigned to the same assignee as the present invention.

For the sake of convenience to the reader, the pertinent portion of the disclosure of copending application No. 875,218 will be set out herein. The defibrillator is structured to be implanted in the patient, and, to that end, all components, including batteries, high voltage generator (including capacitors) and output circuit, logic and control circuitry, and detection circuitry are housed in a metal case inert to body tissue and fluids. Lead/electrode assemblies (including defibrillation patch electrodes of the type described above) for sensing cardiac activity and for delivering the shock impulses to the patient's heart are separably connectable to the defibrillator.

The implantable defibrillator includes a digital control section for storing and executing software instructions and for storing and processing the data for all digital functions of the device, including detection, processing, timing, switching, control and other functions described more fully in copending application Ser. No. 875,218. An analog section is also provided for monitoring the patient's ECG signal information over each cardiac cycle, enhancing that signal information while eliminating noise and other interference through signal filtering and automatic gain control, developing the pulse (truncated exponential) waveforms to be delivered for the defibrillating shocks, and various other functions, also described in the copending application Ser. No. 875,218. The defibrillator further includes battery cells, voltage regulator, and priority power sequencer for supplying power to the various sections of the overall system.

A central microprocessor with associated memory capacity including RAM and ROM is provided for processing and storing data, for programming and other functions, and for supplying the logic control inputs to various sections of the defibrillator. The microprocessor/memory section may be conventionally coupled to programming and data transmission circuitry for receiving program instructions and data from an external programmer of a type utilized for physician control of certain parameters, via an implanted antenna. A crystal oscillator may be used to supply the precise timing signals to the microprocessor/memory section for system operation.

A sense amplifier is preferably used to enhance ECG signals to aid the tracking of signal content of rapidly varying amplitude, such as fibrillation signals. In addition, bandpass filtering may be employed to reduce the amplitude of signals outside the frequency band of interest and to further amplify low frequency (e.g., fibrillation) signals in that band in the absence of normal R-waves.

The power source section of the defibrillator includes high rate battery cells, a voltage regulator and a priority power sequencer. The high rate cells may be any combination of cells capable of delivering sufficient energy to charge the capacitors in the output high voltage section within a prescribed time interval (e.g., 20 seconds or less). The voltage regulator circuit preferably has a voltage divider to provide a 3:1 reduction if three cells are used in series, or a 2:1 reduction if only two cells are employed, and thereby improves power source efficiency. The priority power sequencer is used to assure adequate power is made available to the essential circuit functions such as the control logic during periods when there would otherwise be high current drain on the cells, such as during charge up of the high voltage capacitors in preparation for the delivery the defibrillating shocks.

The leads for sensing electrodes may be electrically monitored by an isolation/protection circuit to protect low voltage, low power components of the system from the high voltage of the defibrillating shocks (or applied from an external defibrillator that may be used on the patient during emergency medical procedures). A suitable protection circuit is disclosed in copending U.S. patent application Ser. No. 799,804, of William Winstrom, entitled "Protection Apparatus for Patient-Implantable Device", filed Nov. 20, 1985, and assigned to the same assignee as the present application.

The principal portion of the implantable defibrillator of interest herein is the isolated high voltage generator and output section. The voltage generator circuitry includes a high voltage oscillator coupled via an isolation transformer to output capacitors for charging the capacitors to the required voltage levels for the defibrillating shocks, under the control of the microprocessor. A low power analog-to-digital (A/D) converter monitors the voltage on the capacitors, and alerts the microprocessor so that the high voltage output level will be set according to the programmed values. In addition, the A/D converter input circuit may be selectively connected by the microprocessor to the power source section of the defibrillator to monitor the battery voltage, to determine the present condition of the cells.

The high voltage generator and output circuit also includes level shifters and isolation transformers to convert the microprocessor-supplied low level logic control signals to the control signal levels required to drive the output switches of that section. The output switches themselves are of low "on" impedance and capable of handling the high voltages and currents being generated, to control the duration and polarity of each output pulse. A short circuit protection circuit is provided to open the output circuit in the event that the current therethrough rises above a predetermined level, to prevent discharge of the capacitors into a very low impedance—such as if the defibrillator patch electrodes were shorted.

Figure 4:
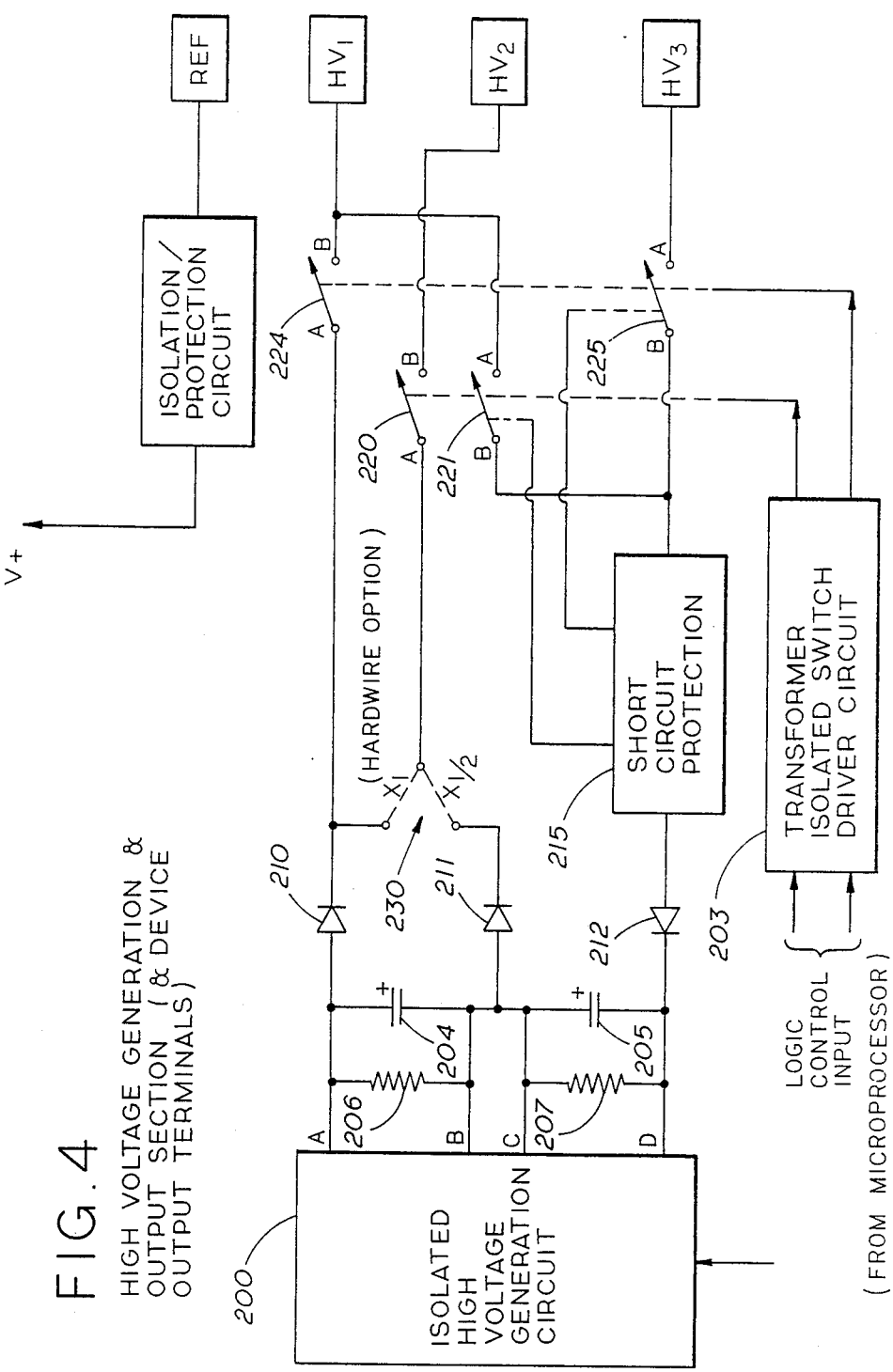
FIGS. 4–7 are circuit diagrams illustrating a suitable high voltage generator and output circuit for an implantable defibrillator capable of generating the biphasic waveforms of the present invention.

Referring now to FIG. 4, the output connections for the defibrillator are designated "REF", "HV1", "HV2" and "HV3". Left ventricular patch electrode 15 (FIGS. 1a and b) is affixed to the epicardium (connected to "REF" and "HV1") and right ventricular patch electrode 12 is affixed to the epicardium (connected to "HV2" and "HV3"). Defibrillation shocks are from patch electrode 15 to patch electrode 12. Alternatively, the patch electrodes may be affixed to the pericardium with the same positioning and connections as set forth immediately above.

As shown in FIG. 4, the high voltage generation and output section of the defibrillator comprises an isolated high voltage generation circuit 200; a transformer isolated switch driver circuit 203; output capacitors 204 and 205 with associated bleeder resistors 206 and 207: protection diodes 210, 211 and 212 an output short circuit protection circuit 215; and two pairs of high voltage output switches 220, 221 and 224, 225. When ventricular fibrillation is detected, the microprocessor enables high voltage generation circuit 200 to charge output capacitors 204 and 205 to a preselected value. After the charging is completed, the prescribed output shock is delivered by closing the appropriate switch pair. For purposes of the present invention, the prescribed output shock is a biphasic waveform in which the first phase is of longer duration than the second phase Depending on how HV1, HV2 and HV3 are connected externally, a variety of output combinations can be accomplished. If HV2 and HV3 are connected together, the closing of switch pair 220, 221 (using hardwire option x1) produces an output voltage of opposite polarity to the voltage generated by closing switch pair 224, 225. The hardwire option 230 enables selection of either a full or half amplitude for the output via switch pair 220, 221. This allows the generation of biphasic output waveforms of approximately half amplitude in one direction and full amplitude in the other direction.

Figure 5:
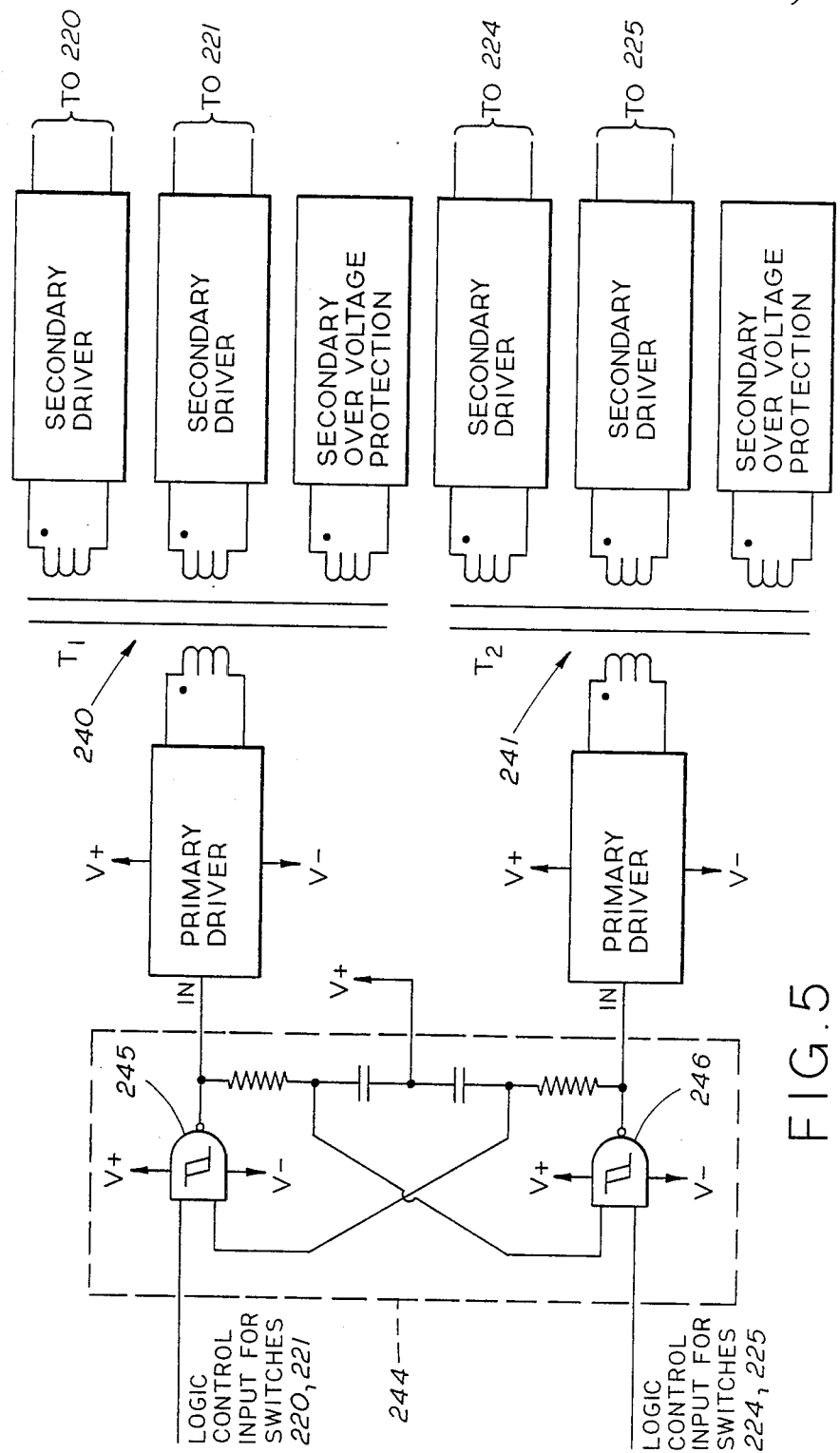

Referring now to FIG. 5, the transformer isolated switch driver circuit 203 comprises transformers 240 and 241, each having one primary driver circuit, two secondary driver circuits and one secondary overvoltage protection circuit. An input circuit 244 assures non-overlap between the signals controlling the pairs of output switches 220, 221 and 224, 225. Level shifted logic circuits 245, 246 respond to logic control inputs from the microprocessor to supply logic inputs to the two primary drivers. The isolation provided by transformers 240 and 241 protects the low voltage low power electronic components from the high voltage outputs.

Figure 6:
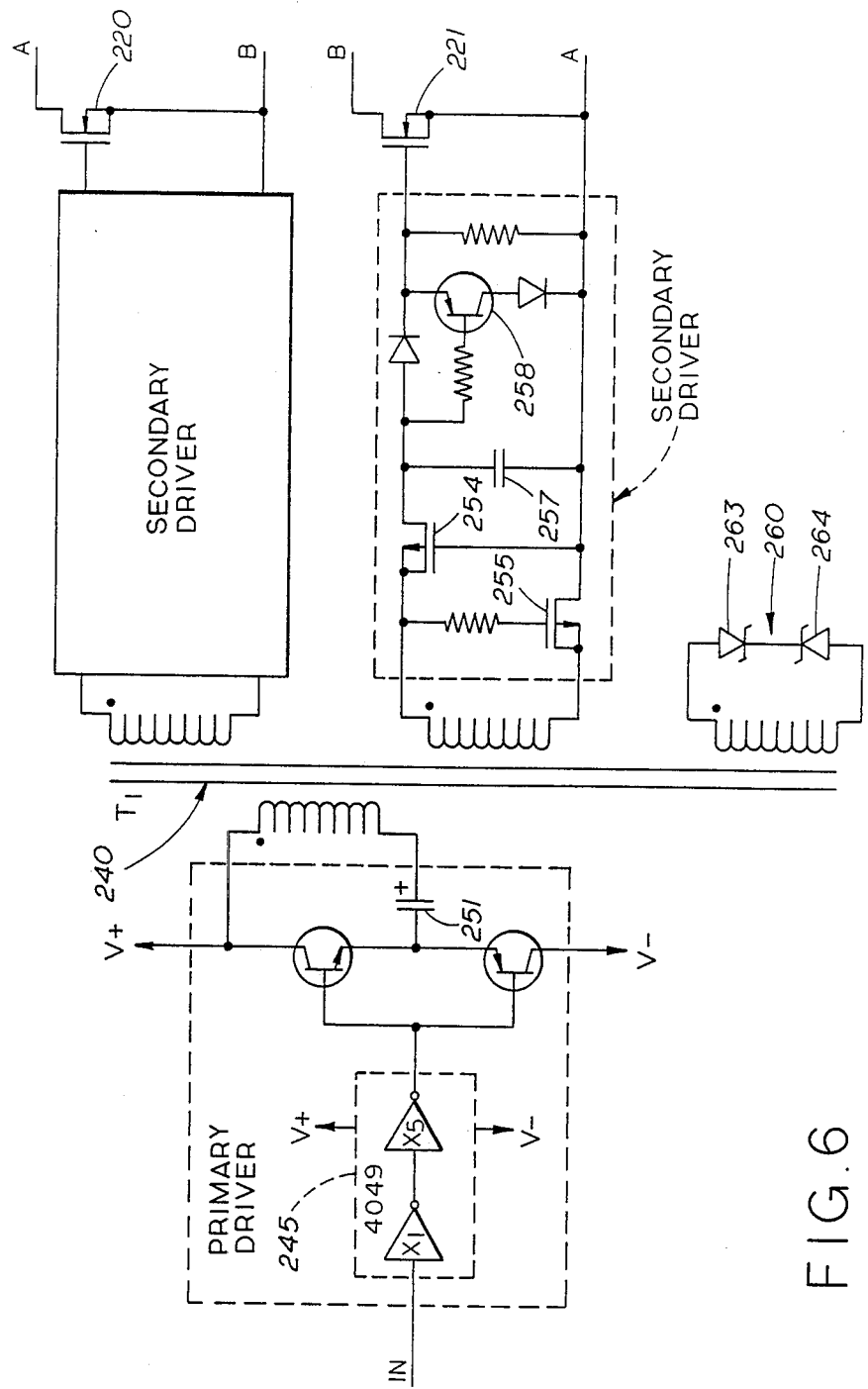

FIG. 6 shows the primary and secondary drivers of each transformer in greater detail. The leading edge of a negative logic pulse at the input of the primary driver causes the negative end of capacitor 251 to be pulled from V+ to V−. This transfers energy from the capacitor to the primary coil winding and consequently to the secondary winding (through the ferromagnetic core on which the windings are wound). The result is a positive voltage across the secondary circuit which turns on P-channel transistor 254 and provides forward bias for the parasitic diode across P-channel transistor 255, charging capacitor 257 and the gate capacitance of N-channel transistor (switch) 221 while holding PNP transistor 258 off. The positive voltage at the gate of transistor 221 turns that switch on (and similarly switch 220, from the corresponding operation of its secondary driver), allowing current to flow from the output switches to the lead/electrode configuration and the patient's heart.

On the trailing edge of the input logic pulse, the negative end of capacitor 251 (which is now fully charged) is pulled to V+, producing a negative voltage across the secondary circuit. This turns on transistor 255 and provides forward bias for the parasitic diode across transistor 264, reverse charging capacitor 257, turning on transistor 258 and dumping the gate capacitance of transistor 221 which turns off that switch (and similarly, switch 220, as a consequence of the corresponding operation of its secondary driver). This disconnects the high voltage capacitors 204, 205 (FIG. 4) from the external load, thus terminating that portion of the shock output pulse waveform. In addition, transistor 258 prevents the gate voltage of transistor 221 from being influenced by capacitively coupled signals impressed on its drain.

The secondary overvoltage protection circuit 260 comprising zener diodes 268 and 264 assures that the voltage applied to the secondary driver of the respective transformer is not large enough to break down any of the transistors in the switch driver circuit. This permits use of larger transformer winding ratios so that circuit performance is not diminished with partial battery depletion. The 4049 inverters 245, 246 are configured to provide the high current drive requirements of the emitter followers they are driving.

Figure 7:
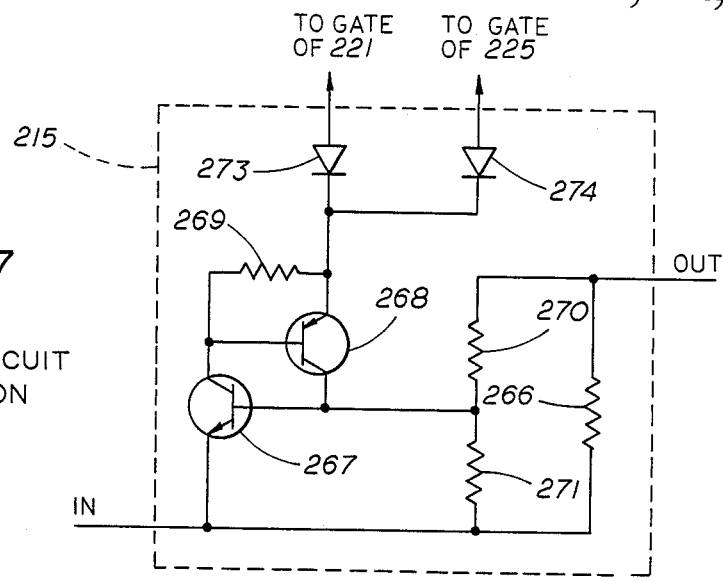

The output short circuit protection circuit 215 of the high voltage generator and output circuit is shown in greater detail in FIG. 7. The protection circuit prevents excessive current flow through (and thus, damage to)

the output switches. Current from the high voltage output capacitors 204, 205 must flow through low impedance resistor 266 to the output switches the external load (the patch electrodes and the heart). Transistors 267 and 268 and resistor 269 form a discrete silicon controlled rectifier (SCR). If the current through resistor 266 increases enough to turn on transistor 267 through the divider consisting of resistors 270, 271, the SCR latches on and pulls down on the gates of output switches 221 and 225 (through diodes 278 and 274), discharging their respective gate capacitances and turning them off. This causes the voltage across resistor 266 to fall because of the reduced current through that resistor, and once the current through the SCR returns to a very low value, the SCR turns off and is ready to be triggered again.

Referring now to FIG. 8, isolated high voltage generation circuit 200 provides the means to charge the high voltage output capacitors 204, 205 to the preselected voltage level, based on logic control inputs from the microprocessor. The capacitor voltage monitor 220 comprises a digital-to-analog (D/A) converter which is also controlled by the microprocessor processor. The output of the D/A converter goes to one input of a voltage comparator. The other input to the comparator may be connected to a divided down version of the output capacitor voltage for controlling the charge voltage, or to the battery (V−) for battery condition monitoring. A high impedance referencing resistor 283 provides a reference to the V+ voltage.

When configured for capacitor charging, the microprocessor presets the desired voltage value and enables the high voltage oscillator 287 to charge up the capacitors using the flyback circuit comprising transformer 288, N-channel transistor 290, battery cells 291, 292 and 293, filter capacitors 295, 296 and 297, and high voltage oscillator circuit 287. To accomplish this, transistor 290 is turned on and current is allowed to flow through the primary winding of transformer 288. When this current has risen sufficiently, transistor 290 is abruptly turned off and a very large flyback voltage develops across the primary (and consequently across the secondaries) of the transformer. The voltages across the secondaries are half wave rectified by diodes 302 and 304, to provide a single direction charge transfer to the capacitors 204 and 205 (FIG. 12), forcing them to charge to a DC voltage.

When the voltage monitor comparator 280 signals the microprocessor that the requested voltage has been reached, the high voltage oscillator 287 is disabled and the output is delivered. The high voltage oscillator is also intermittently disabled by the low voltage regulator circuit to insure priority to the control circuitry power source. Fuse 305 provides protection against overheating of the battery cells 291, 292 and 293 because of excessive current drain caused by a circuit failure. Diodes 810, 311 and 312 provide a low impedance path around a respective battery cell if it becomes depleted. This allows more efficient high voltage charging in the event that one cell has failed. The third secondary of transformer 288 provides a positive voltage source for the high voltage oscillator circuit.

Figure 9:
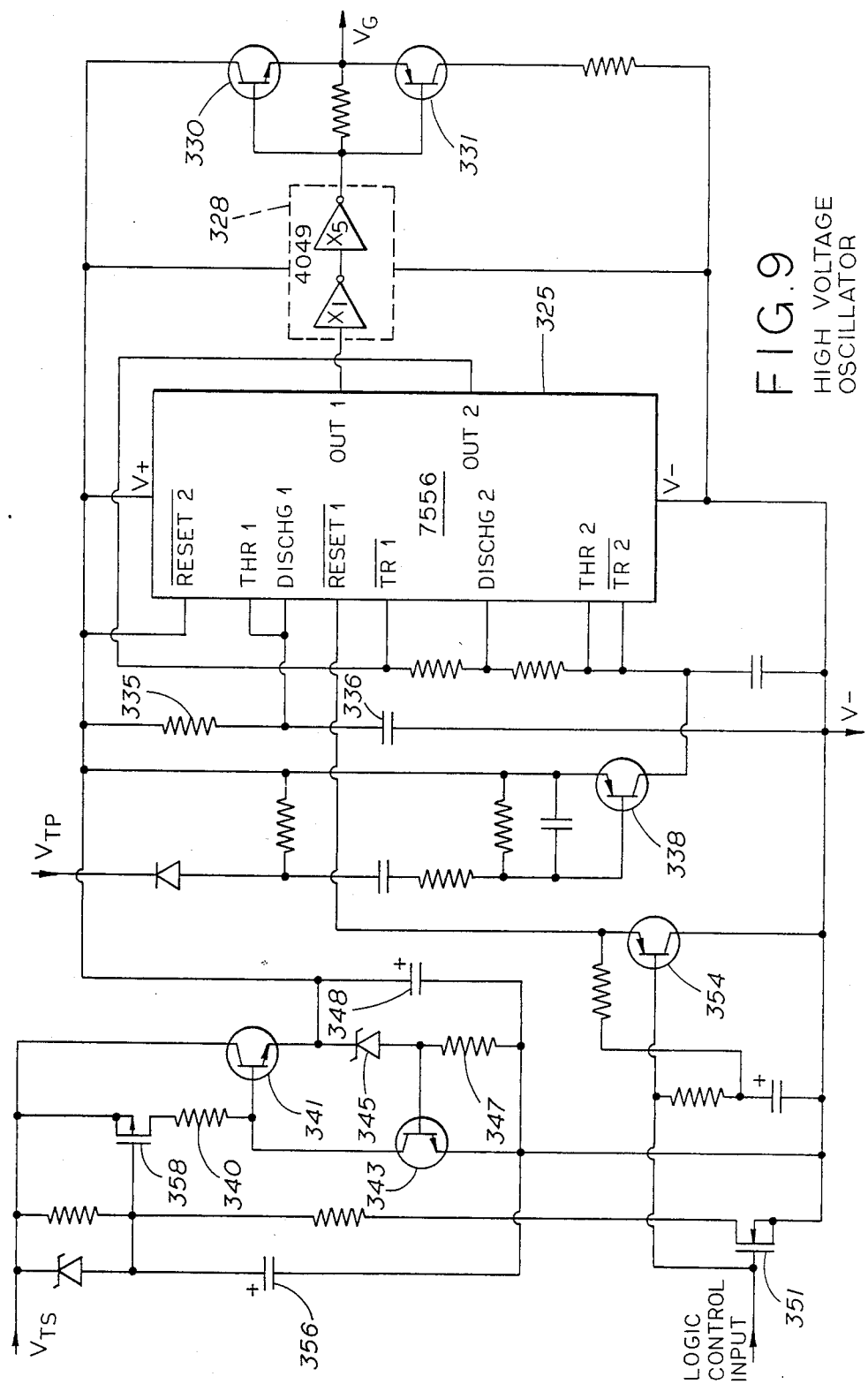

High voltage oscillator circuit 287, illustrated in greater detail in the circuit diagram of FIG. 9, includes a 7556 timer IC 325 which provides the output pulse train that drives the gate of N-channel transistor 290 (FIG. 8). A high capacitance load driver, comprising inverter 328 and transistors 330 and 331, is used to drive the gate capacitance of transistor 290 This circuit provides rapid turn-off of transistor 290, which improves the efficiency of the flyback operation. The latter transistor is also selected to have a very low drain to source "on" impedance since switch drop losses may greatly diminish efficiency.

One-half of timer 325 is configured to run astable at a preset rate determined by resistors 332 and 333 and capacitor 334. The output of this timer triggers the second half of timer 325, which is configured to produce an output pulse having a duration determined by resistor 335 and capacitor 336. This output controls the switch driver circuit. As the output capacitors charge up, energy is transferred out of the transformer core more quickly. This causes the negative transition of the flyback voltage (occurring at $V_{TP}$) to occur sooner. If this transition occurs before the astable portion of timer 325 times out, transistor 338 is turned on, resetting this timer. In this state, the oscillator continues to speed up as the capacitors complete their charging, producing a more efficient operating condition (since the fixed rate would have resulted in wasted time).

A regulated voltage (generated by resistor 340, transistors 341 and 343, diode 345, resistor 347 and capacitor 348) is provided to the timer IC 325 to make circuit performance independent of battery voltage (over the usable range of the cells). The positive secondary voltage (VTS) provides the regulator circuit with ample voltage overhead to make this possible. To enable the high voltage logic circuit, a positive logic signal is applied to the gate of N-channel transistor 351. This turns that transistor on, providing power to the circuit and removing the reset condition (at RESET1 of timer 325). If the low voltage regulator requests that the high voltage oscillator be temporarily disabled, the logic signal at the gate of transistor 351 is brought low which immediately resets the timer 325 (via transistor 354) but does not remove the power to this circuit until capacitor 356 charges up to shut transistor 358 off. This allows short interrupts of the oscillator without disturbing power which also improves the circuit efficiency.

Referring now to FIG. 10, the voltage regulator/power priority sequencer section comprises five switches 371–375 (controlled by low power logic) to charge up a capacitor 377 to a preset value ($V_{reg}$). Capacitors 378 and 379 are much smaller than capacitor 377 and are used in conjunction with capacitor 377 to divide the supply voltage by three, and to transfer charge to the latter capacitor a small amount at a time. When capacitor 377 is being charged, switches 371–375 are switching between their respective A and B states. When the regulated voltage monitor senses that capacitor 377 is at the appropriate voltage level, it signals the switch control logic to go to the standby mode where switches 371, 372 and 374 stay in state B and switches 378 and 375 go to their C state to stop the charging of capacitor 377. The regulated voltage monitor then watches $V_{reg}$ and, via the switch control logic, guarantees that $V_{reg}$ is maintained at this preset value by enabling the charge mode whenever it is needed.

If the supply voltage drops below a level which will support this division by three (i.e., $V_{reg}$ could not be properly regulated), the supply voltage monitor signals the switch control logic section 382 which changes to the direct regulation mode. In this mode, switches 372 and 374 are in state B, switches 373 and 375 are in state C, and switch 371 switches between states B and C, charging capacitor 377 directly from the supply voltage. This mode is much more inefficient but is designed to assure that $V_{reg}$ generation has high priority (even if more power is required).

In addition, if the regulated voltage monitor is requesting that capacitor 377 be charged, switch control logic 382 generates a logic inhibit signal and sends it to the high voltage oscillator circuit (a circuit that causes major drain on the supply when active) and disables its operation until the $V_{reg}$ voltage is back to the desired level. This guarantees that $V_{reg}$ (which provides power to the control logic, including the logic that controls the high voltage operation) is given priority to assure safe operation.

Figure 11:
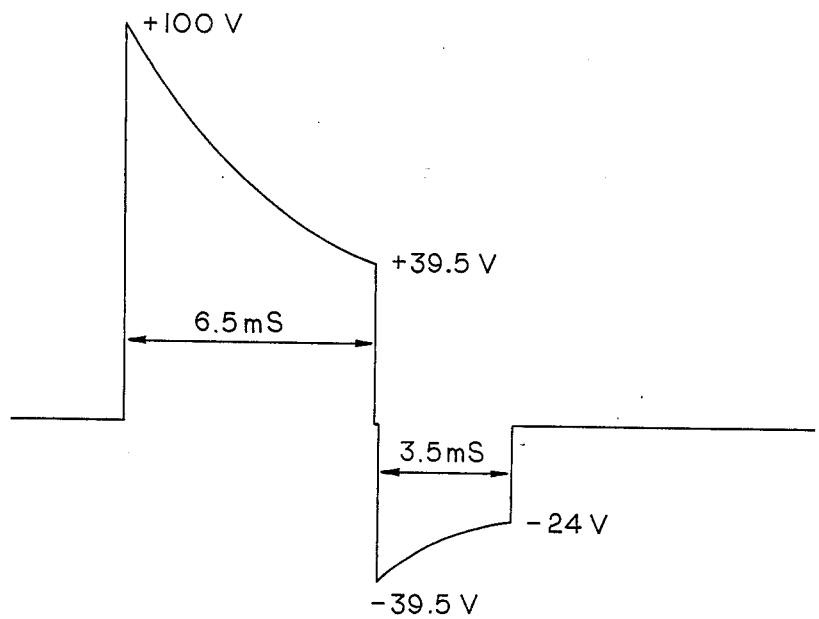
FIG. 11 illustrates a biphasic waveform consisting of truncated exponential pulses having relative durations, polarities, and voltage levels according to the invention.

FIG. 11 illustrates a biphasic waveform having a configuration according to the present invention, which is generated by the defibrillator high voltage generator. Initial voltage magnitude is determined by the logic control inputs supplied by the microprocessor to the isolated high voltage generation circuit 200 (FIG. 4). All logic control inputs determining waveform parameters are derived from the programming instructions of the physician, using an external programmer. The microprocessor logic control inputs to the transformer isolated switch driver circuit 203 set the duration and polarity of each phase of the defibrillation shock shown in FIG 11. All of this is accomplished in the manner described earlier herein. Switch pairs 220, 221 and 224, 225 are closed and opened in alternation (with the hardwire option 230 in the XI mode) for placing the full voltage on the capacitors across the output lead assembly. It will be understood that the switches are preferably of the solid state type, rather than mechanical switches as depicted in FIG. 4.

The defibrillation lead/electrode connections are as described in the earlier discussion of the circuit of FIG. 4, above. The biphasic waveform is applied via the output circuit of the generator to the lead assembly, patch electrodes and the heart, based on preselected first and second phase durations and polarities, and utilizing 175 microfarad high voltage capacitances discharging into a 40 ohm load, in this example. The first phase is set to have a 6.5 millisecond duration and the second phase is set to have a 8.5 millisecond duration as shown in FIG. 11. Both phases are truncated exponential pulses, the first phase commencing at +100 V and decaying according to the circuit time constant including the RLC components of the circuit and the impedance presented by the lead/electrode configuration and the heart. At the time switches 224, 225 are opened, the voltage magnitude of the first phase of the shock has decayed to approximately +39.5 V, and the switches 220, 221 are then closed to cause the second phase to commence at about the same voltage but opposite polarity, i.e., about −39.5 V and decaying after the 3.5 ms duration to approximately −24 V.

It is more convenient to specify initial voltage magnitude of the first phase, than to specify the amount of energy to be delivered in the shock. However, energy content can be specified from a knowledge of certain parameters, such as the aforementioned time constant of the circuit, initial voltage level setting, and load impedance.

Although a presently preferred embodiment and method of practicing the invention has been described, it will be apparent from the foregoing description that variations may be implemented without departing from the spirit of the invention. For example, the invention may be used for cardioversion of certain tachyarrhythmias or as part of a comprehensive therapy generator. Accordingly, it is intended that the invention be limited only by the appended claims.

We claim:

1. A method of defibrillating a heart in fibrillation, comprising the steps of:
   detecting the onset of fibrillation of the heart, and
   applying to the fibrillating heart a biphasic waveform having only a first phase and a second phase, each phase of the waveform being characterized by a predetermined time duration and by a predetermined polarity and magnitude of voltage, in which the duration of the first phase of the applied waveform is greater than the duration of the second phase.

2. The method of claim 1, in which:
   the initial voltage magnitude of the first phase of the applied biphasic waveform is greater than the initial voltage magnitude of the second phase.

3. The method of claim 1, in which:
   the step of applying is performed by delivering the biphasic waveform to a pair of patch electrodes affixed over and contoured to conform substantially to the surface of the right and left ventricles, respectively, of the heart.

4. The method of claim 3, in which:
   the patch electrodes are affixed to the epicardium.

5. The method of claim 3, in which:
   the patch electrodes are affixed to the pericardium.

6. The method of claim 3, in which:
   the left ventricular patch electrode is used as the cathode for the first phase of the applied biphasic waveform, and as the anode for the second phase.

7. A method of terminating ventricular fibrillation by direct internal defibrillation, comprising the steps of:
   detecting the onset of ventricular defibrillation,
   responding to that detection by applying a first defibrillation shock directly to the ventricles, in which the shock is a voltage of predetermined magnitude, polarity and duration,
   immediately thereafter applying a second defibrillation shock directly to the ventricles, in which the second shock is a voltage of opposite polarity and shorter duration than the initially applied shock, and
   ceasing the delivery of any further defibrillation shocks after the second shock, pending detection of the activity of the heart in response to the first and second shocks.

8. The method of claim 7, in which:
   the second shock is of lower magnitude than the initially applied shock.

9. A method of defibrillating the heart, comprising the steps of:
   placing a first patch electrode over the right ventricle of the heart, configured to conform substantially to the shape and size of the surface of the right ventricle,
   placing a second path electrode over the left ventricle of the heart, configured to conform substantially to the shape and size of the surface of the left ventricle in spaced relationship to the first patch electrode to form a uniform gap between confronting borders of the two patch electrodes in the region of the ventricular septum, while encompassing a substantial portion of the ventricular myocardium between the two patch electrode, toward establishing a uniform potential gradient field through out the entire ventricular mass when a defibrillating electrical waveform is applied to the electrodes, and applying a defibrillating electrical waveform constituting a biphasic shock having a first phase of longer duration than the second phase thereof, to the electrodes.

10. The method of claim 8, in which the first phase is a voltage of greater magnitude than the second phase.

11. The method of claim 10, further including making the gap between the confronting borders of the two patch electrodes of sufficient width to prevent shunting of current between the confronting borders during application of the defibrillating waveform.

12. The method of claim 11, further including making the gap between the confronting borders of the patch electrodes of sufficient width to accommodate the ventricular septum therein, to establish preferential current flow through one ventricle across the septum to the free wall of the other ventricle during application of a defibrillating waveform to the electrodes.

13. The method of claim 12, further including making the gap between the confronting borders of the patch electrodes of sufficient width to accommodate the left anterior descending coronary artery and the posterior descending coronary artery therein, to avoid vascular damage from the application of defibrillating waveforms to the electrodes.

14. An implantable defibrillator, comprising means for detecting fibrillation, electrical generating means responsive to the detection of fibrillation for producing a biphasic waveform in which each phase is characterized by an electrical impulse of predetermined polarity, magnitude and duration, the first phase being of greater duration and magnitude than and of opposite polarity to the second phase, and means for delivering said waveform to provide electrical shock to the ventricles of the heart.

15. The implantable defibrillator of claim 14, wherein said generating means produces biphasic waveforms in which each phase is a truncated exponential pulse.

16. The implantable defibrillator of claim 8 wherein said delivering means comprises a pair of patch electrodes, one having a size and shape to be placed over the right ventricle and the other having a size and shape to be placed over the left ventricle, the pair of electrodes cooperating to encompass virtually the entire ventricular myocardium therebetween.

* * * * *

UNITED STATES PATENT AND TRADEMARK OFFICE
CERTIFICATE OF CORRECTION

PATENT NO. : 4,821,723
DATED : April 18, 1989
INVENTOR(S) : Baker, Jr., et al.

It is certified that error appears in the above-indentified patent and that said Letters Patent is hereby corrected as shown below:

Column 7, line 53: delete "82" and insert therefor -- 32 --.

Column 7, line 57: delete "84" and insert therefor -- 34 --.

Column 16, line 61 (in claim 9): insert a comma after the word "ventricle".

Column 16, line 68 (in claim 9): delete "through out" and insert therefor -- throughout --.

Column 13, line 46: delete "FIG. 12" and insert therefor -- FIG. 4 --.

Column 16, line 36 (in claim 7): delete "defibrillation" and insert therefor -- fibrillation --.

Signed and Sealed this

Twenty-seventh Day of January, 1998

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 4,821,723
DATED : April 18, 1989
INVENTOR(S) : Baker, Jr., et al.

It is certified that error appears in the above-identified patent and that said Letters Patent is hereby corrected as shown below:

Column 17, line 7 (in claim 10): delete "8" and insert therefor -- 9 --,

Column 18, line 19 (in claim 16): delete "8": and insert therefor -- 15 --.

Signed and Sealed this

Twenty-fourth Day of March, 1998

Attest:

BRUCE LEHMAN

Attesting Officer

Commissioner of Patents and Trademarks